United States Patent [19]
Schmieding

[11] Patent Number: 6,027,523
[45] Date of Patent: Feb. 22, 2000

[54] SUTURE ANCHOR WITH ATTACHED DISK

[75] Inventor: Reinhold Schmieding, Naples, Fla.

[73] Assignee: Arthrex, Inc., Naples, Fla.

[21] Appl. No.: 09/132,550

[22] Filed: Aug. 11, 1998

Related U.S. Application Data

[60] Provisional application No. 60/061,146, Oct. 6, 1997, and provisional application No. 60/070,099, Dec. 31, 1997.

[51] Int. Cl.[7] .................................................. A61B 17/04
[52] U.S. Cl. ............................................. 606/232; 606/73
[58] Field of Search ....................................... 606/232, 72

[56] References Cited

U.S. PATENT DOCUMENTS

| | | | |
|---|---|---|---|
| 4,632,100 | 12/1986 | Somers et al. | 606/73 |
| 5,156,616 | 10/1992 | Meadows et al. | 606/232 |
| 5,306,290 | 4/1994 | Martins et al. | 606/232 |
| 5,370,662 | 12/1994 | Stone et al. | 606/232 |
| 5,630,824 | 5/1997 | Hart | 606/139 |
| 5,665,112 | 9/1997 | Thal | 606/232 |
| 5,720,765 | 2/1998 | Thal | 606/232 |

*Primary Examiner*—Gary Jackson
*Attorney, Agent, or Firm*—Ostrolenk, Faber, Gerb & Soffen, LLP

[57] ABSTRACT

A suture anchor assembly for attachment of tissue to bone includes a suture anchor having a distal end and a proximal end, the proximal end having an opening. A filament strand is looped through the opening and is attached at either end to a disk. The disk has a central opening that accommodates a suture anchor driver. The driver engages the suture anchor for installation through the tissue and into the underlying bone. As the suture anchor is installed into bone, tissue is approximated to the bone by the captured disk. Traction suture attached to the disk allows testing of the installation, and retrieval of the assembly in the event of failure during installation.

21 Claims, 5 Drawing Sheets

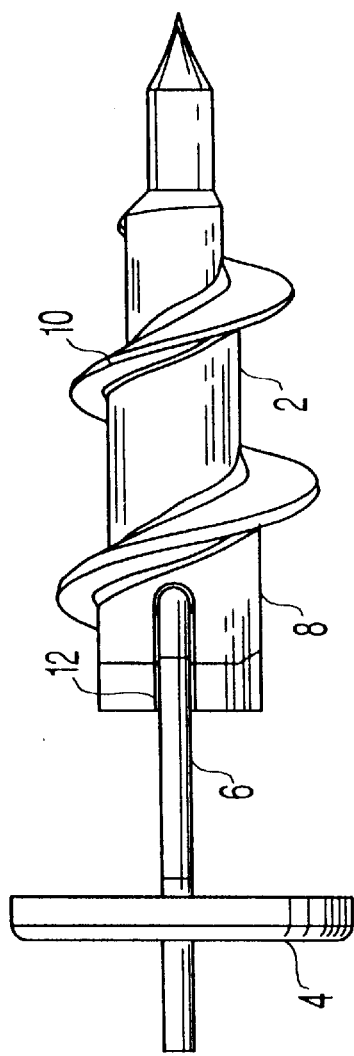
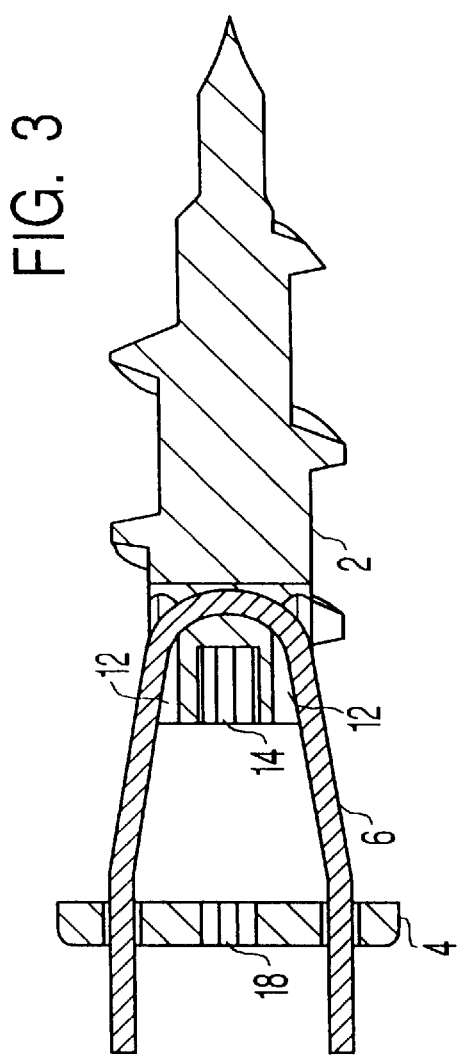
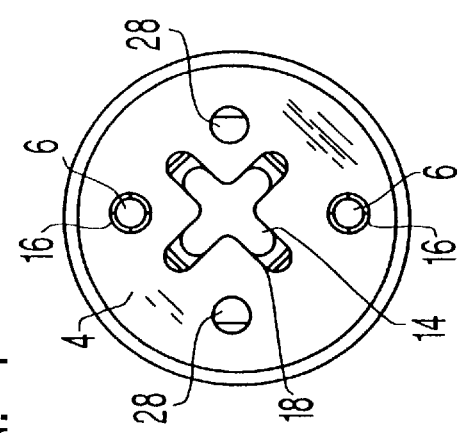
FIG. 2
FIG. 3
FIG. 4

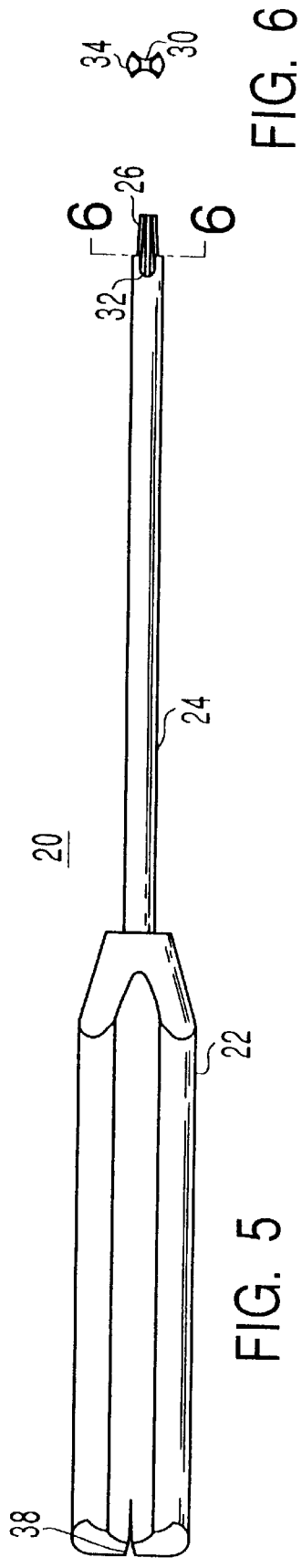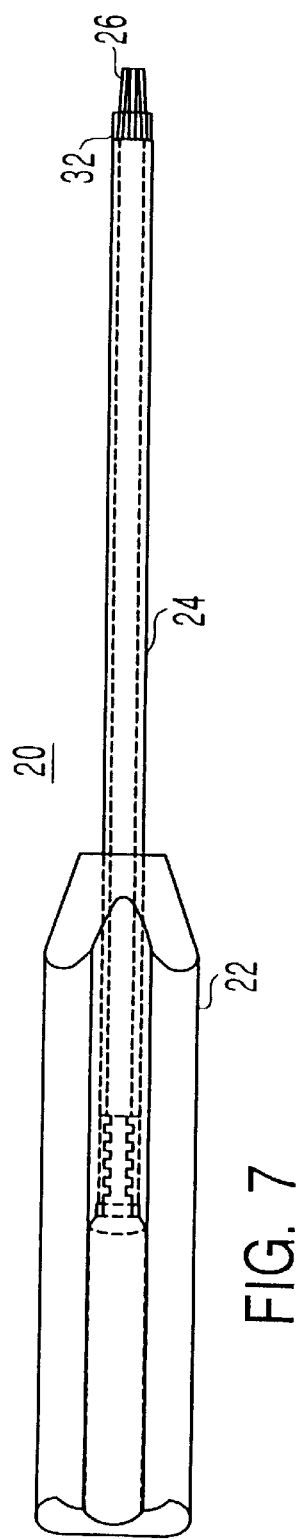

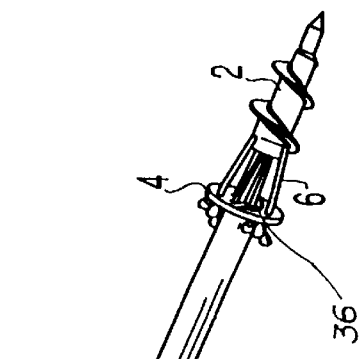
FIG. 8
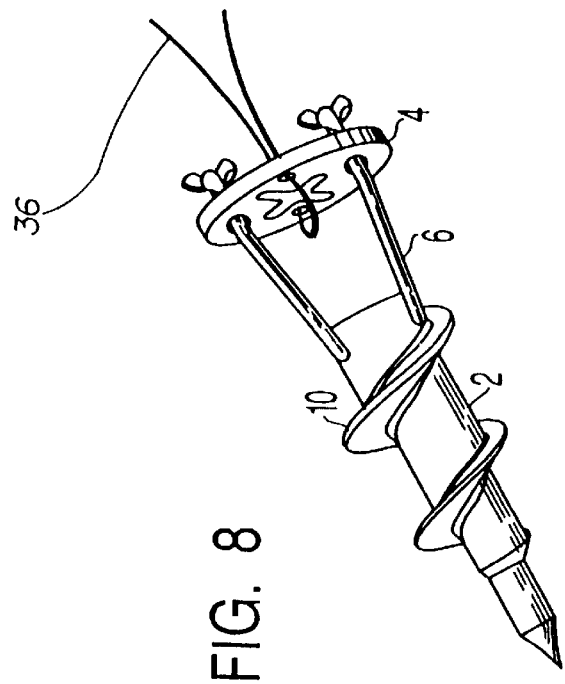
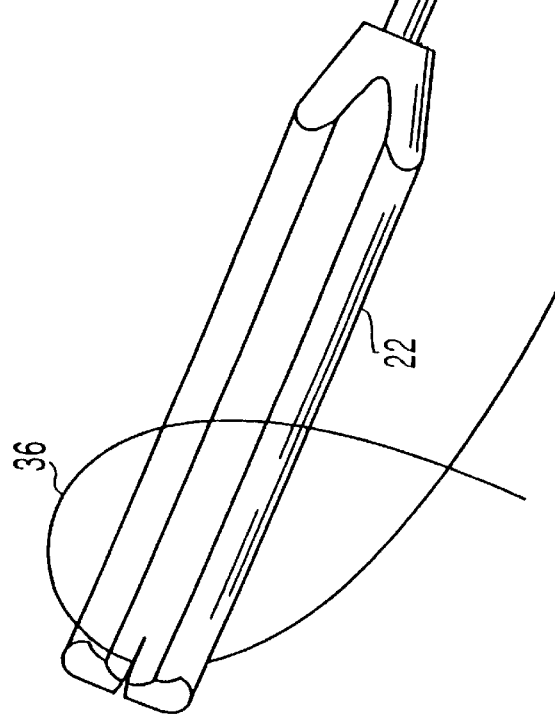
FIG. 9

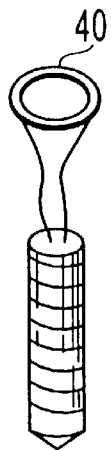 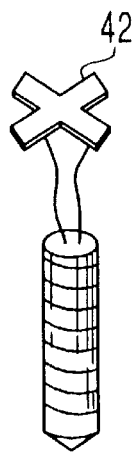 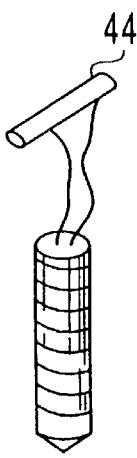 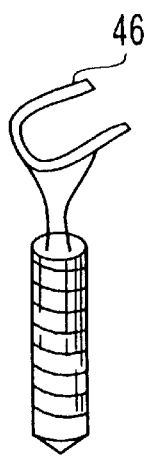
FIG. 10  FIG. 11  FIG. 12  FIG. 13
 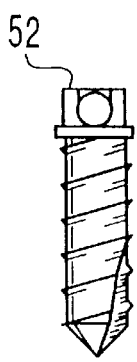 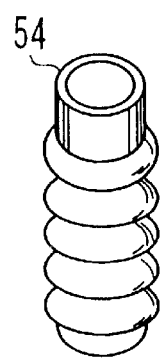 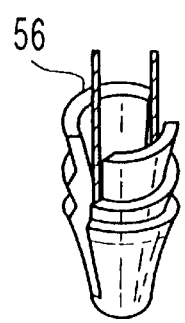
FIG. 14  FIG. 15  FIG. 16  FIG. 17

SUTURE ANCHOR WITH ATTACHED DISK

This application claims the benefit of U.S. Provisional Application Ser. No. 60/061,146, filed Oct. 6, 1997, and U.S. Provisional Application Ser. No. 60/070,099, filed Dec. 31, 1997, the disclosures of which are incorporated herein by reference.

BACKGROUND OF THE INVENTION

1. Field of the Invention

The present invention relates to surgical fixation of soft tissue to bone. More specifically, the present invention relates to apparatus and methods for securing soft tissue to bone using a suture anchor equipped with a tissue-fixation disk.

2. Description of the Related Art

When soft tissue tears away from bone, reattachment becomes necessary. Various devices, including sutures alone, screws, staples, wedges, and plugs have been used to reattach soft tissue to bone.

Recently, suture anchors have been developed for this purpose. Some suture anchors are designed to be inserted into a pre-drilled hole. Others are self-tapping and have screw threads.

U.S. Pat. No. 4,632,100 discloses a cylindrical suture anchor which includes a drill bit at a leading end for boring a hole in a bone. The drill bit at the leading end is followed by a flight of threads for securing the anchor into the hole bored in the bone by the drill bit. U.S. Pat. No. 5,370,662 discloses a self-tapping suture anchor having a flight of threads around a solid body. U.S. Pat. No. 5,156,616 discloses a similar suture anchor having an axial opening for holding a knotted piece of suture.

U.S. application Ser. No. 08/954,206, filed Oct. 20, 1997, the disclosure of which is incorporated herein by reference, discloses a corkscrew suture anchor which is designed to provide enhanced pull-out strength in cancellous bone.

The devices disclosed in the above-cited patents anchor suture to bone, but require the surgeon to tie a knot in the suture arthroscopically in order to achieve fixation of the soft tissue to the bone.

U.S. Pat. No. 5,720,765 to Thal, issued Feb. 24, 1998, discloses suture anchors with pre-attached, tissue-anchoring means. These devices lack various features of the present invention, including, for example, means for engaging the anchor and the anchoring means with a driver. In addition, Thal '765 does not disclose means for holding the suture anchor on a driver or for testing pull-out strength of the inserted anchor.

Thus, the need exists for soft tissue fixation devices that do not require arthroscopic knot tying for fixation, and which provide benefits such as advantageous means for inserting and testing the fixation devices.

SUMMARY OF THE INVENTION

The present invention overcomes the deficiencies of the prior art, such as those noted above, by providing a suture anchor combined with a tissue retaining device, such as a disk, plate or rod. In a preferred embodiment, the tissue retaining device is a disk which is associated with the suture anchor by a loop of material such as a monofilament or suture.

Advantageously, a socket is formed at the proximal end of the suture anchor. A suture anchor driver with a drive end having a complimentary shape fits into the socket to engage the suture anchor. The driver also fits through the tissue-retaining disk by way of a correspondingly-shaped opening formed centrally in the disk. Accordingly, the anchor and the tissue-retaining disk turn simultaneously when rotated by the driver.

A loop of fiber material captures the tissue-retaining device at the proximal end of the suture anchor prior to installation. The suture preferably is looped through an eye disposed on or formed through the proximal end of the suture anchor. Upon installation of the suture anchor through soft tissue and into bone, the tissue-retaining device contacts the soft tissue, approximating the soft tissue to the bone in which the anchor is installed.

Additionally, one or more traction line can be attached to the tissue-retaining device to extend proximally, preferably through a cannulated driver. During installation, the traction line is used to hold the suture anchor and retaining device securely on the distal end of the driver. Once installed, the traction line can be utilized to test sufficiency of the installation, to reverse the installation, or can be removed for completion of the repair.

Other features and advantages of the present invention will become apparent from the following description of the invention which refers to the accompanying drawings.

BRIEF DESCRIPTION OF THE DRAWINGS

FIG. 2 is a top plan view of a suture anchor assembly according to the present invention.

FIG. 3 is a cross-sectional side elevation of a suture anchor assembly according to the present invention.

FIG. 4 is a proximal end view of a suture anchor assembly according to the present invention.

FIG. 5 is a side elevation of a driver for a parachute suture anchor according to the present invention.

FIG. 6 is a sectional view of the driver of FIG. 6, taken at the line VI—VI.

FIG. 7 is a top plan view of the driver of FIG. 5.

FIG. 8 is a perspective view of the suture anchor assembly of the present invention.

FIG. 9 is a schematic perspective view of the suture anchor assembly loaded on the driver of the present invention.

FIG. 10 is a schematic of an alternative suture anchor assembly according to the present invention.

FIG. 11 is a schematic of an additional alternative embodiment of the suture anchor assembly of the present invention.

FIG. 12 is a schematic of an additional alternative embodiment of the suture anchor assembly of the present invention.

FIG. 13 is a schematic of an additional alternative embodiment of the suture anchor assembly of the present invention.

FIG. 14 is a schematic representation of an alternative suture anchor for use in the present invention.

FIG. 15 is a schematic representation of another alternative suture anchor for the present invention.

FIG. 16 is a schematic representation of an additional alternative suture anchor for the present invention.

FIG. 17 is a schematic representation of a further additional alternative suture anchor for the present invention.

DETAILED DESCRIPTION OF THE PREFERRED EMBODIMENTS

Figure 1:
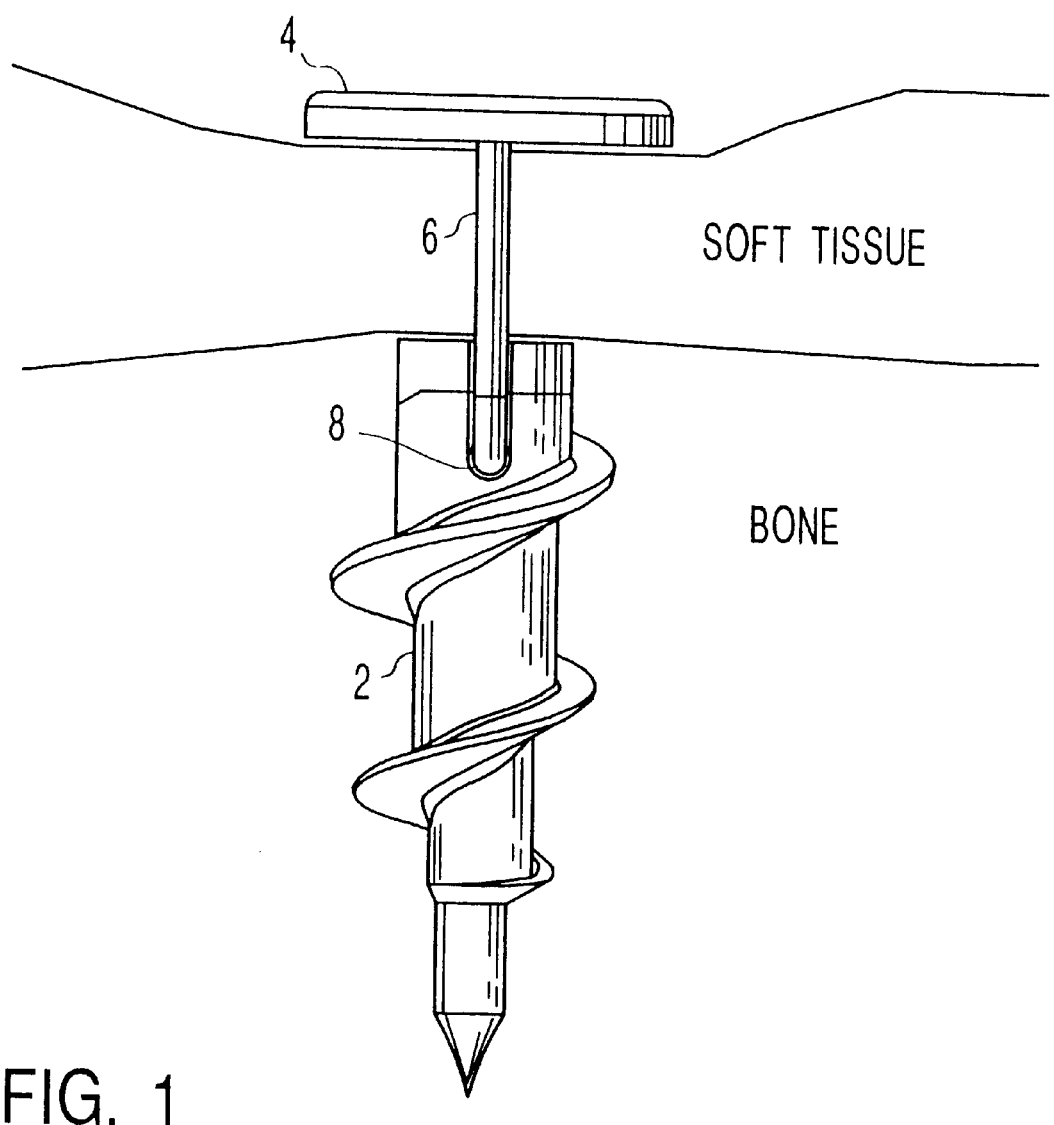
FIG. 1 is a schematic elevation of a parachute suture anchor assembly which has been installed according to the present invention.

Referring initially to FIG. 1, a preferred embodiment of a suture anchor assembly according to the present invention is shown diagrammatically in side elevation, having been installed in the body at a repair site so as to approximate soft tissue to bone.

The suture anchor assembly includes a threaded suture anchor 2, which is associated with a disk 4 by a length of polypropylene filament 6. The filament passes through an eye 8 formed in the proximal end of suture anchor 2. The free ends of filament 6 are secured to disk 4 using knots, cement, insert-molding, or other means of disk attachment, as described more fully below. In a preferred embodiment, the filament is knotted, and a drop of polyacrylamide or similar cement is used to secure the knot.

Each of the components is formed of a biocompatible and/or biosorbable material. Preferably, anchor 2 is formed of titanium. Alternatively, anchor 2 also can be formed of biosorbable materials. Either or both of disk 4 and suture 6 can be formed of a biosorbable material, such as PLLA. It is noted, however, that if filament 6 is biosorbable, disk 4 also should be biosorbable. Disk 4 alternatively can be made of a plastic material such as Delrin.

Referring to FIGS. 2 and 3, suture anchor 2 has eye 8, which has been formed through the suture anchor at approximately the same level as the most-proximal flight of thread 10. Grooves 12, provided on either side of the proximal end of suture anchor 2, extend proximally from eye 8. Grooves 12 accept and protect filament 6 as it passes along the sides of the proximal end of suture anchor 2.

The suture anchor 2 is formed such that the minor, inner diameter of the suture anchor body narrows radially from the proximal end to the distal end, to form a conical wedge. In addition, the thickness of thread 10 narrows continuously from the proximal end to the distal end, particularly along the thread portion located toward the outer edge of the thread, forming a helical wedge. The major diameter of the suture anchor body is established rapidly beginning at the distal end, and remains substantially constant along the remainder of the thread length proceeding proximally along the suture anchor. As a result, the suture anchor body and the suture anchor threads continuously wedge themselves into the bone as the anchor is advanced during insertion.

The proximal end of the thread terminates in an exposed, flat face. Once seated below the surface of the bone, the edges of the flat face will engage the bone, as a further deterrent to backout of the anchor.

Referring also to FIG. 4, cruciform drive socket 14 is formed in the proximal end of anchor 2. The socket preferably is tapered inward distally, and the socket is formed to depth that provides sufficient strength while not intersecting with eye 8.

A driver for the suture anchor seats snugly in drive socket 14. The loop formed by filament 6 passing through eye 8 of suture anchor 2 passes around either side of the drive socket 14 formed in the anchor, as shown in FIG. 3, providing a compact and sturdy proximal end for driving the bone anchor and for securing the tissue-retaining disk.

Disk 4 is provided with a pair of holes 16 into which free ends of filament 6 are inserted for capturing disk 4. The filament 6 can be adhered to or within the disk 4, or tied in knots as shown in FIG. 8, to capture the disk 4 onto the proximal end of suture anchor 2. Advantageously, filament 6 can slide through eye 8, such that disk 4 articulates to conform to the surface of the approximated tissue.

Cruciform driver opening 18 is provided centrally on disk 4 and aligns with cruciform drive socket 14. For installation of the parachute suture anchor, the tip of a suture anchor driver has a complimentary shape and is received through opening 18 and into socket 14, as described more fully below.

Referring to FIGS. 5, 6, and 7, a preferred embodiment of a driver 20 for installing a parachute suture anchor according to the present invention is shown. Driver 20 has a cannulated handle 22 coupled to a cannulated driver shaft 24. The distal tip 26 of the driver, shown in cross-section in FIG. 6, is shaped to compliment both the socket 14 of suture anchor 2 and the central opening 18 formed in disk 4.

Accordingly, driver 20 rotationally engages both the suture anchor 2 and the disk 8, such that the disk and the suture anchor turn simultaneously with the driver, avoiding tension on filament 6. Accordingly, no twisting or abrading of the filament 6 which captures the disk 4 occurs during insertion of the fixation device into bone.

Grooves 30 formed by the driver tip provide relief areas for the filament 6 which passes along the side of the driver tip, further minimizing the amount of frictional wear and abrasive stress experienced by the filament as the anchoring device is installed. In addition, cut-outs 32 formed at the distal end of cannulated shaft 24, proximal to the tip 26, provide relief for knots or other attachment means for filament 6 formed on the proximal side of disk 4, as described more fully below.

The cannulated driver 20 is provided with openings 34 near the distal end which accept traction line 36. Traction line 36 is looped through holes 28 formed in disk 4, as illustrated in FIG. 8, and is passed through the cannulated driver 20. Tension on traction line 36 applied proximally holds the fixation device to the driver tip, as shown in FIG. 9, the traction suture having been retained in notches 38 formed on proximal end of handle 22. See FIG. 5.

The fixation device also is held on the tip 26 due to a slight taper in the tip so that the suture anchor assembly can be snugged onto driver 20.

Traction line 36 also can be used to confirm fixation strength after installation. Further, traction line 36 can be used to retrieve the disk or the entire fixation device in the event of device failure during installation. Once the installation and fixation strength are determined to be adequate, traction line 36 easily is removed by pulling on one end of the traction line.

Preferably, the parachute fixation device is provided in various sizes and lengths of filament to accommodate fixation to various bone types and through various thicknesses of soft tissue.

Those of skill in the art will recognize that alternative embodiments of the fixation device of the present invention can be accomplished with various types of tissue retaining means substituted for disk 8, such as those shown in FIGS. 10–13, including a ring 40, cross 42, straight bar 44, and bended bar 46. In addition, various types of suture anchors, such as those shown in FIGS. 14–17, including smooth spike 50, barbed spike 52, cylindrical threaded anchor 54, and expanding anchor 56, can be used to anchor the assembly of the present invention.

The present invention has been described in relation to particular embodiments thereof. Many other variations, modifications, and other uses will become apparent to those skilled in the art. Accordingly, the invention is to be limited not by the disclosure herein, but only by the appended claims.

What is claimed is:

1. A suture anchor assembly for attachment of tissue to bone, the suture anchor assembly comprising:
   a suture anchor having a distal end and a proximal end, the proximal end having an opening for receiving at least one filament, and a socket having a shape for receiving a suture anchor driver;
   at least one filament looped slidingly through the opening and having a first end and a second end; and
   a tissue-retaining device attached to the first end and the second end of the filament and provided with a central aperture having a shape similar to the shape of the socket for receiving the suture anchor driver.

2. The suture anchor assembly of claim 1, further comprising at least one traction line extending proximally from the tissue-retaining device.

3. The suture anchor assembly of claim 1, wherein the tissue-retaining device is a disk.

4. The suture anchor assembly of claim 1, wherein the filament is attached to the tissue-retaining device using a knot.

5. The suture anchor assembly of claim 1, wherein the filament is attached to the tissue-retaining device using injection molding.

6. The suture anchor assembly of claim 1, wherein the filament is attached to the tissue-retaining device using an adhesive.

7. A suture anchor assembly and driver combination comprising:
   a suture anchor having a distal end and a proximal end, the proximal end having an opening, and a driving attachment for receiving a suture anchor driver;
   at least one filament looped slidingly through the opening and having a first end and a second end;
   a tissue-retaining device attached to the first end and the second end of the filament, the tissue-retaining device having a central aperture sized and shaped so as to accept the driver; and
   a driver having a distal end and a proximal end, the distal end being disposed through the central aperture of the tissue-retaining device and engaging the driving attachment of the suture anchor.

8. The combination of claim 7, wherein the central aperture of the tissue-retaining device engages the driver such that the suture anchor and the tissue-retaining device turn simultaneously when rotated by the driver.

9. The combination of claim 7, further comprising at least one traction line extending proximally from the tissue-retaining device.

10. The combination of claim 7, wherein the tissue-retaining device is a disk.

11. The suture anchor assembly of claim 7, wherein the filament is attached to the tissue-retaining device using a knot.

12. The suture anchor assembly of claim 7, wherein the filament is attached to the tissue-retaining device using injection molding.

13. The suture anchor assembly of claim 7, wherein the filament is attached to the tissue-retaining device using an adhesive.

14. A method of attaching tissue to bone using a suture anchor assembly including a suture anchor having a distal end and a proximal end, the proximal end having an eye, at least one filament looped slidingly through the eye and having a first end and a second end, and a tissue-retaining device attached to the first end and the second end of the suture strand said tissue-retaining device being attached to a traction suture, the method comprising the steps of:
   inserting the suture anchor assembly through the tissue;
   coupling the suture anchor assembly to a driver;
   applying tension to the traction suture to hold the suture anchor assembly to the driver; and
   installing the suture anchor assembly into bone, using the driver, to approximate the tissue to the bone.

15. A suture anchor assembly for attachment of tissue to bone, the suture anchor assembly comprising:
   a suture anchor having a distal end and a proximal end, the proximal end having an opening;
   at least one filament looped slidingly through the opening and having a first end and a second end; and
   a tissue-retaining device attached to the first end and the second end of the filament by respective knots in the filament.

16. The suture anchor assembly of claim 15, further comprising at least one traction line extending proximally from the tissue-retaining device.

17. The suture anchor assembly of claim 15, wherein the tissue-retaining device is a disk.

18. The suture anchor assembly of claim 15, the suture anchor further comprising a socket formed on the proximal end having a shape for receiving a suture anchor driver.

19. The suture anchor assembly of claim 18, wherein the disk is provided with a central aperture having a shape similar to the shape of the socket formed in the suture anchor for receiving the suture anchor driver.

20. A method of attaching tissue to bone using a suture anchor assembly including a suture anchor having a distal end and a proximal end, the proximal end having an eye and a socket having a shape, at least one filament looped slidingly through the eye and having a first end and a second end, and a tissue-retaining device attached to the first end and the second end of the suture strand and having a central aperture, the shape of the central aperture being similar to the shape of the socket, the method comprising the steps of:
   coupling the suture anchor assembly to a distal end of an installation driver by inserting the distal end of the driver through the central aperture of the tissue retaining device and into the socket of the suture anchor;
   inserting the suture anchor assembly through the tissue using the driver; and
   installing the suture anchor assembly into bone by turning the assembly with the driver to approximate the tissue to the bone.

21. The method of claim 20, wherein the suture anchor assembly further comprises at least one traction line extending proximally from the tissue-retaining device, the method comprising the further step of holding the suture anchor assembly onto the driver using the traction line.

* * * * *